`US012414824B2`

(12) United States Patent
Suppa

(10) Patent No.: US 12,414,824 B2
(45) Date of Patent: Sep. 16, 2025

(54) METHOD FOR OPERATING A MEDICAL NAVIGATION SYSTEM FOR AN IMAGE-GUIDED SURGICAL PROCEDURE

(71) Applicant: OLYMPUS CORPORATION, Tokyo (JP)

(72) Inventor: Per Suppa, Hamburg (DE)

(73) Assignee: OLYMPUS CORPORATION, Tokyo (JP)

( * ) Notice: Subject to any disclaimer, the term of this patent is extended or adjusted under 35 U.S.C. 154(b) by 350 days.

(21) Appl. No.: 17/951,242

(22) Filed: Sep. 23, 2022

(65) Prior Publication Data

US 2023/0122724 A1 Apr. 20, 2023

Related U.S. Application Data

(60) Provisional application No. 63/257,730, filed on Oct. 20, 2021.

(51) Int. Cl.
| | | |
|---|---|---|
| *A61B 34/10* | (2016.01) | |
| *A61B 34/20* | (2016.01) | |
| *A61B 90/00* | (2016.01) | |

(52) U.S. Cl.
CPC .............. *A61B 34/20* (2016.02); *A61B 90/36* (2016.02); *A61B 2034/105* (2016.02); *G06T 2207/20084* (2013.01)

(58) Field of Classification Search
None
See application file for complete search history.

(56) References Cited

U.S. PATENT DOCUMENTS

| | | | |
|---|---|---|---|
| 11,170,526 B2 * | 11/2021 | Tosun | G06T 7/38 |
| 11,298,195 B2 * | 4/2022 | Ye | B25J 9/1689 |
| 11,995,820 B2 * | 5/2024 | Kim | A61B 6/5223 |
| 2021/0196398 A1 * | 7/2021 | Ye | A61B 1/000094 |
| 2022/0084234 A1 * | 3/2022 | Lee | G06V 10/803 |
| 2022/0160443 A1 * | 5/2022 | Spykerman | G16H 30/40 |

(Continued)

FOREIGN PATENT DOCUMENTS

| | | | | |
|---|---|---|---|---|
| CN | 117836776 A | * | 4/2024 | ............. A61B 34/10 |
| WO | WO-2021030536 A1 | * | 2/2021 | ............. A61B 34/20 |

(Continued)

*Primary Examiner* — Ted W Barnes
(74) *Attorney, Agent, or Firm* — Scully, Scott, Murphy & Presser, P.C.

(57) ABSTRACT

A method for operating a medical navigation system for an image-guided surgical procedure including: training a first artificial neural network on a set of surgical image video data of a target object of a patient representing a video image, and identifying the structure of the target object; training a second artificial neural network on at least one virtual three-dimensional target object model of the target object and identifying the structure of the virtual three-dimensional target object model by the identified structure of the target object; training a third artificial neural network by the identified structure of the target object and the structure of the virtual three-dimensional target object model and aligning the identified structure of the target object, with the structure of the corresponding target object of the virtual three-dimensional target object model, which is identified by the second artificial neural network.

20 Claims, 2 Drawing Sheets

(56) References Cited

U.S. PATENT DOCUMENTS

2023/0034101 A1* 2/2023 Yardibi ................ G06N 3/09
2024/0169579 A1* 5/2024 Luengo Muntion ... G16H 20/40

FOREIGN PATENT DOCUMENTS

| WO | WO-2023144570 A1 * | 8/2023 | ........... G06V 10/764 |
| WO | WO-2023239513 A1 * | 12/2023 | ............. A61B 34/10 |
| WO | WO-2024141970 A1 * | 7/2024 | ............. A61B 34/10 |

* cited by examiner

METHOD FOR OPERATING A MEDICAL NAVIGATION SYSTEM FOR AN IMAGE-GUIDED SURGICAL PROCEDURE

CROSS-REFERENCE TO RELATED APPLICATION

The present application is based upon and claims the benefit of priority from U.S. Provisional Application No. 63/257,730 filed on Oct. 20, 2021, the entire contents of which is incorporated herein by reference.

BACKGROUND

Field

The present disclosure relates to a method for operating a medical navigation system for an image-guided surgical (IGS) procedure. Moreover, the present disclosure relates to a computer-readable storage medium having stored thereon a computer program for causing a computing device to perform a method for operating a medical navigation system.

PRIOR ART

Surgeries with a laparoscope, also known as laparoscopic surgeries or laparoscopies, offer a number of advantages compared to traditional open surgeries, e.g., smaller incisions and a shorter recovery time. In laparoscopic surgery, intraoperative navigation plays a crucial role. However, there are a number of difficulties involved in this kind of navigation. The organ cannot be touched, so that haptic feedback is unavailable to the surgeon. Thus, the position of a tumour cannot be felt. In addition, laparoscopic ultrasound is the only available technique to visualize sub-surface structures, e.g., veins, arteries and tumours, under the surface of the target organ. Laparoscopic ultrasound usually only provides 2D images which need to be integrated in the surgeon's mind to refer to the actual position of the 2D ultrasound slice in 3D space.

In order to solve this problem, preoperative image data of the organ, for example a computer tomography (CT) image or a magnetic resonance (MR) image, is often captured before the operation. This preoperative image data is transformed into a three dimensional model of the organ, which is then aligned with the intraoperative laparoscopic image data, so that additional information from the pre-operative image can be added to the intraoperative image. The alignment of the model with the intraoperative image is called image registration.

SUMMARY

It is an object to provide an improved navigation for an image-guided surgical procedure.

Such object can be solved by a method for operating a medical navigation system for an image-guided surgical (IGS) procedure comprising:
  training of a first artificial neural network on a set of surgical image video data of a target object of a patient, which represents a video image, and identifying the structure of the target object of the patient;
  training of a second artificial neural network on at least one virtual three-dimensional target object model of the target object (of the patient) and identifying the structure of the virtual three-dimensional target object model (virtual 3D target object model) by the structure of the target object of the patient, which is identified by the first artificial neural network;
  training of a third artificial neural network by the identified structure of the target object of the patient and the structure of the virtual three-dimensional target object model and aligning the structure of the target object of the patient, which is identified by the first artificial neural network, with the structure of the corresponding target object of the virtual three-dimensional target object model, which is identified by the second artificial neural network.

The present embodiments use a virtual 3D model to establish a correspondence between the minimal-invasive video image of a target object of a patient and a corresponding virtual 3D target object model which in turn is used to automatically align the pose or orientation of the virtual 3D target object model to the pose of the target object of the patient, like a target organ or the like, on a video screen based on the detection of anatomical landmarks, detected by the first artificial neural network on the captured video image data or the set of the video image data of the real target object.

Therefore, it is possible to display a patient-specific virtual 3D target object model directly on the same screen as the laparoscopic video image of the real target object model. Hence, the method for operating a medical navigation system for an image-guided surgical procedure establishes, such as automatically, a correspondence between the virtual 3D target object model and the video image based on anatomical landmark detection of the (real) target object. Therefore, the method can assist a surgeon in the spatial navigation during the procedure.

A benefit of the method is to support the surgeon in finding the corresponding position of structures or landmarks of the target object in both, the intraoperative video image, e.g., laparoscopic video image, and the preoperative virtual 3D target object model. If a position of a landmark or of a structure of the (real) target object is detected by the first artificial neural network, the virtual 3D target object model enables a surgeon to discover the spatial relationship of several key anatomical structures or landmarks with respect to each other and thus assists with spatial navigation.

A first artificial neural network for object detection is trained on a set of surgical video or image data of the (real) target object in order to detect certain important anatomical landmarks or the structure of the target object, which can be in a static mode or in a real-time mode. Furthermore, a second artificial neural network for object detection is trained on at least one virtual 3D target object model of the target object in order to learn the corresponding representations of the (anatomical) landmarks or structures of the target object that were learned by the first artificial neural network on the set of surgical video image data. A third artificial neural network is then trained to match the pose or orientation of the (anatomical) landmarks or the structure of the target object. Accordingly, the third artificial neural network learns how to align the (anatomical) landmarks or the structure of the (real) target object, detected by the first artificial neural network, and the corresponding (anatomical) landmarks or structure of the virtual 3D target object model(s), detected by the second artificial network, with each other.

According to another embodiment, the second artificial neural network can be trained on a data set of a series of corresponding virtual three-dimensional target object models of the target object, wherein the structure of the virtual three-dimensional target object models are identified by the structure of the target object of the patient, which is identified by the first artificial neural network. The second artificial neural network can be trained on a large number of virtual three-dimensional target object models of the target object, like more than 10 or 30 or 100 virtual three-dimensional target object models of the target object.

Above all, in case an important anatomical landmark or structure of the (real) target object is detected on the surgical, for example laparoscopic, video image data during the procedure, then the second artificial network can be triggered to identify the corresponding (anatomical) landmarks or structure on the virtual 3D target object model. In case of a match in both imaging modalities, the landmarks or the structures can be, for example, highlighted on the intraoperative video data, wherein the virtual 3D target object model, such as with the corresponding highlighted structure on the virtual 3D target object model, enables the surgeon to identify and understand the anatomy on the virtual 3D model in a quick and convenient way.

Moreover, the method can provide the possibility to recognize the current pose or orientation of the virtual 3D target object model on the surgical screen. In this context, the method allows to detect, such as automatically, whether the anatomical landmark of interest is not visible in the virtual 3D target object model in this pose or orientation because it may be hidden behind other structures.

If the method determines if the landmark or structure in the virtual 3D target object model is hidden behind other structures, the method can reposition the virtual 3D target object model in a way that the (anatomical) landmarks or structures are clearly visible on the screen. Moreover, according to an embodiment, the method can be configured to reposition the virtual 3D target object model in a way, that the orientation or the pose of the virtual 3D target object model matches with the orientation or the pose of the (real) target object, e.g., an organ or the like, in the video image, such as on demand. Accordingly, the method can provide a solution for a core challenge in the active research field of image registration in the field of surgery, such as in laparoscopic surgery, as the amount of anatomical information during the procedure is very limited by the restricted field of view of the laparoscope.

Furthermore, the anatomical landmarks of interest in the surgery image and the virtual 3D target object model do not need to look similar due to a deformation of the organ surface intraoperatively.

The third artificial neural network, which can be a deep learning-based artificial neural network, can be used in a further aspect to learn the pose or orientation of an anatomical structure or landmark in space and to establish a correlation with the surgery image of the target object to reorient the virtual 3D target model accordingly.

The set of surgical image video data can be captured by a video processor, wherein the video processor can be configured as a CMOS senor or a CCD sensor.

The set of surgical image video data can be displayed on a monitor.

According to a further aspect, the set of surgical image video data can be displayed on a monitor and the structure of the virtual three-dimensional target object model, which is identified by the second artificial neural network, can be displayed, such as simultaneously, on a common or one monitor.

The set of surgical image video data can be displayed in a predetermined orientation and the structure of the virtual three-dimensional target object model, which is identified by the second artificial neural network, can be displayed in an orientation, which corresponds or aligns with the predetermined orientation of the surgical image video data.

Moreover, according to another aspect of the method, a landmark, which can be automatically detected in the surgical image video data and can be detected by the first artificial neural network, can trigger the second artificial neural network for training on the virtual three-dimensional model.

In a further aspect, the landmark, which can be automatically detected, in the set of surgical image video data can be detected by the first artificial neural network in a static mode or in real-time.

Hence, according to a further development of the method, a detected landmark in the set of surgical image video data can be highlighted and displayed, such as on a monitor.

The second artificial neural network can be configured to be trained on virtual three-dimensional models of the target object of the patient in order to learn and identify a corresponding landmark of the landmark, which can be anatomical and which can be identified by the first artificial neural network, in the structure of the virtual three-dimensional target object model.

Pursuant to an embodiment of the method, in case that the corresponding landmark in the structure of the virtual three-dimensional target object model cannot be displayed due to a hidden pose of the corresponding landmark in the structure of the virtual three-dimensional target object model, the structure of the virtual three-dimensional target object model can be repositioned such that the structure of the virtual three-dimensional target object model with the corresponding landmark is displayed on a monitor.

The corresponding landmark in the structure of the virtual three-dimensional target object model can be highlighted and displayed, such as on a monitor.

According to another aspect, the third neural network can be configured to be trained to match a pose of the landmark, which can be anatomical, in the set of surgical image video data in order to align the structure of the target object of the patient, which is identified by the first artificial neural network, with the structure of the virtual three-dimensional target object model, which is identified by the second artificial neural network.

The first artificial neural network can be an object recognition network, wherein the object recognition network can be configured to learn representations, which can be intraoperative representations, of anatomical structures of the target object of the patient. For example, such object recognition networks like Yolo, InceptionV3 etc. can be used for the detection of anatomical structures of the target object of the patient.

The second artificial neural network can be an object recognition network, wherein the object recognition network can be configured to learn representations of anatomical structures of the target object of the patient in different virtual three-dimensional models.

In addition, the third artificial neural network can be configured to determine world coordinates of the different virtual three-dimensional model with respect to the orientation of the anatomical structures of the target object of the patient in the virtual three-dimensional model.

According to another embodiment, a 3D engine, such as a 3D rendering machine, can be provided, wherein the 3D engine can be configured to display the world coordinates of the different virtual three-dimensional model with respect to the orientation of the anatomical structures of the target object of the patient in the virtual three-dimensional model.

Rendering engines such as Unity, BabylonJS or ThreeJS etc. can be used for the third artificial neural network. The 3D engine can be configured to perform a transformation of local model coordinates to world coordinates.

Such object can be further solved by a computer-readable storage medium having stored thereon a computer program for causing a computing device to perform a method for operating a medical navigation system while performing an image-guided surgical (IGS) procedure, the computer program comprising a plurality of code sections is configured to carry out the above described method. In order to avoid repetitions, reference is expressly made to the above.

Such object can be further solved by a method for operating a medical navigation system for an image-guided surgical (IGS) procedure comprising:
   training of a first artificial neural network on surgical image video data of a target object of a patient and identifying the structure of the target object of the patient;
   acquiring a segmentation layer of a predetermined identified structure of the target object of the patient; and
   training of a further artificial neural network by the structure of the target object of the patient, identified by the first artificial neural network, and the predetermined identified structure of the target object of the patient, provided by the segmentation layer, and aligning the structure of the target object of the patient, identified by the first artificial neural network, with the predetermined structure of the corresponding target object, provided by the segmentation layer.

The set of surgical image video data can be captured by a video processor, wherein the video processor can be configured as a CMOS senor or a CCD sensor.

According to another aspect, the set of surgical image video data can be displayed on a monitor.

The set of surgical image video data can be displayed on a monitor and the predetermined structure of the target object, provided by the segmentation layer, can be displayed, such as simultaneously, on a same monitor.

The set of surgical image video data can be displayed in a predetermined orientation and the predetermined structure of the target object, provided by the segmentation layer, can be displayed in an orientation, which corresponds or aligns with the predetermined orientation of the surgical image video data.

An embodiment of the method provides that a landmark is detected in the surgical image video data, such as being automatically detected and detected by the first artificial neural network can be detected by the first artificial neural network in a static mode or in real-time.

The detected landmark in the set of surgical image video data can be highlighted and displayed, such as on a monitor.

In one embodiment of the method the segmentation layer can comprise meta data of a computed tomography image of the target object of the patient, which can be captured, wherein the meta data can represent the predetermined identified structure of the target object of the patient. The segmentation layer can also be named as annotation, which comprises meta data of a computed tomography image of the target object of the patient, which can be captured.

In case that the predetermined identified structure of the target object of the patient cannot be displayed due to a hidden pose of the predetermined identified structure of the target object of the patient, the predetermined identified structure of the target object of the patient can be repositioned such that the predetermined identified structure of the target object of the patient is displayed on a monitor.

Moreover, the further neural network can be configured to be trained to match a pose of the landmark, which can be anatomical, in the set of surgical image video data in order to align the structure of the target object of the patient, which can be identified by the first artificial neural network, with the predetermined identified structure of the target object of the patient, provided by the segmentation layer.

The first artificial neural network can be an object recognition network, wherein the object recognition network can be configured to learn representations of key anatomical structures, which can be intraoperative, of the target object of the patient.

The further artificial neural network can be configured to determine world coordinates of the different virtual three-dimensional model with respect to the orientation of the anatomical structures of the target object of the patient in the virtual three-dimensional model.

Furthermore, a 3D engine, such as a 3D rendering machine, can be provided, wherein the 3D engine can be configured to display the world coordinates of the different virtual three-dimensional model with respect to the orientation of the anatomical structures of the target object of the patient in the virtual three-dimensional model.

Such object can be further solved by providing a computer-readable storage medium having stored thereon a computer program for causing a computing device to perform a method for operating a medical navigation system while performing an image-guided surgical (IGS) procedure, the computer program comprising a plurality of code sections configured to carry out a method as described above.

The embodiments provide a deep-learning based automatic correspondence search and alignment of a surgery video image of a target object of a patient with a virtual 3D target object models or with a segmentation layer of a predetermined identified structure of the target object of a patient in order to improve the assistance of a surgeon in the spatial navigation during an image-guided surgical (IGS) procedure.

BRIEF DESCRIPTION OF THE DRAWINGS

Further characteristics will become apparent from the description of the embodiments together with the claims and the included drawings. Embodiments can fulfill individual characteristics or a combination of several characteristics.

The embodiments are described below, without restricting the general intent of the invention, based on exemplary embodiments, wherein reference is made expressly to the drawings with regard to the disclosure of all details that are not explained in greater detail in the text. In the drawings.

DETAILED DESCRIPTION

Figure 1:
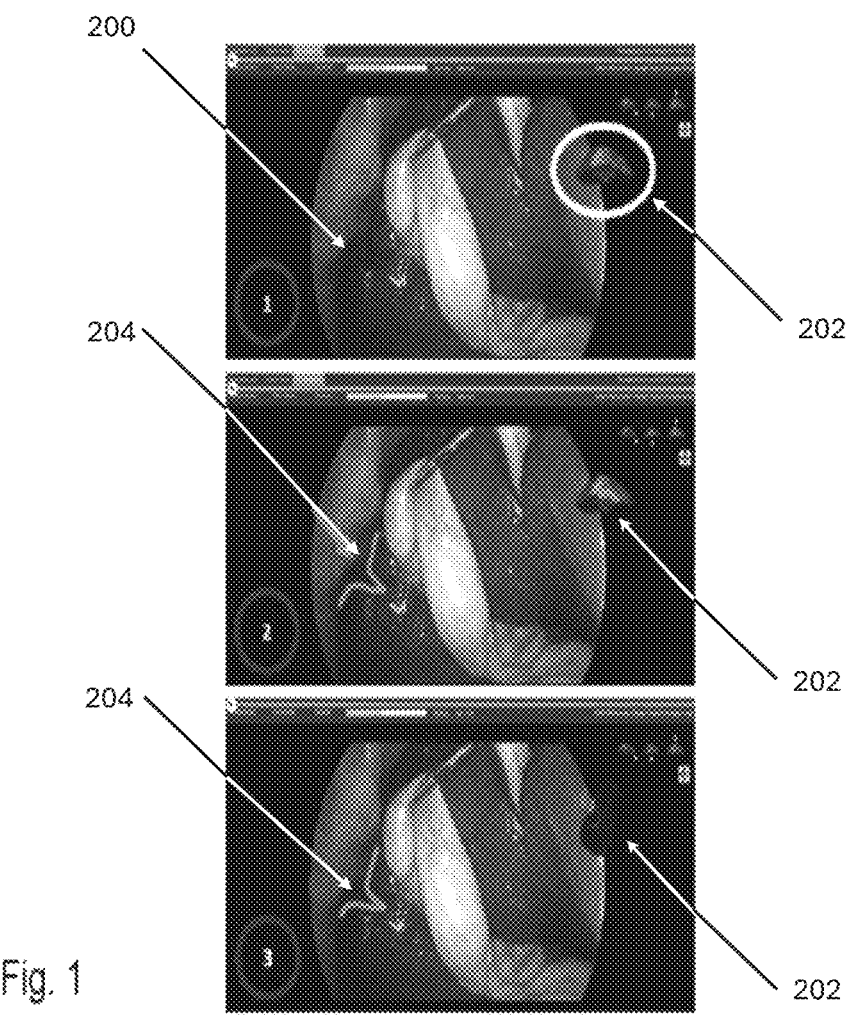
FIG. 1 schematically illustrates three images of a laparoscopic surgery of a liver with a display of a virtual 3D model of the liver.

FIG. 1 shows schematically three examples, which are taken from a laparoscopic liver surgery. All images show an image of a liver 200 (as a target object of a patent) during a surgery with a display of a virtual 3D model of the liver 202 (as 3D target object model) in the upper right corners of a monitor, such as a surgical monitor.

In the upper image 1 of FIG. 1, the virtual 3D model 202 is displayed on a surgical monitor. The virtual 3D model 202 is displayed on the laparoscopic video screen encircled in FIG. 1 in the upper image 1.

By means of a first artificial neural network, an anatomical structure in the laparoscopic image of a real liver captured by a video sensor is detected. The detected anatomical structure 204 is shown in the middle image 2 in the video image. The detected anatomical structure 204 is marked with a V-shaped mark and an arrow on the left side of the (middle) image 2 of FIG. 1.

A second artificial neural network is then used and/or triggered, wherein the second artificial neural network is configured to take the information about the anatomical structure that was detected in the video image as input and to detect the same structure on the virtual 3D model 202 (see small right arrow).

The middle image 2 in the middle indicates a match, where the notch of the liver (detected anatomical structure) 204 at the position of the falciform ligament was detected by the first artificial neural network in the laparoscopic video image (highlighted and with an arrow on the left side) and the same anatomical landmark structure was detected by the second artificial neural network on the virtual 3D model 202 as well (highlighted and with an arrow on the right side).

Afterwards a third artificial neural network is used and configured to align the virtual 3D model 202 of the liver (as target object) with the position of the detected anatomical structure 204 of the liver in the laparoscopic image, as shown in the bottom image 3.

The bottom image 3 of FIG. 1 shows the case in which the third artificial neural network estimates the parameters for repositioning of the virtual 3D model 202 in a way that it aligns with the intraoperative pose (or orientation) of the liver.

Figure 2:
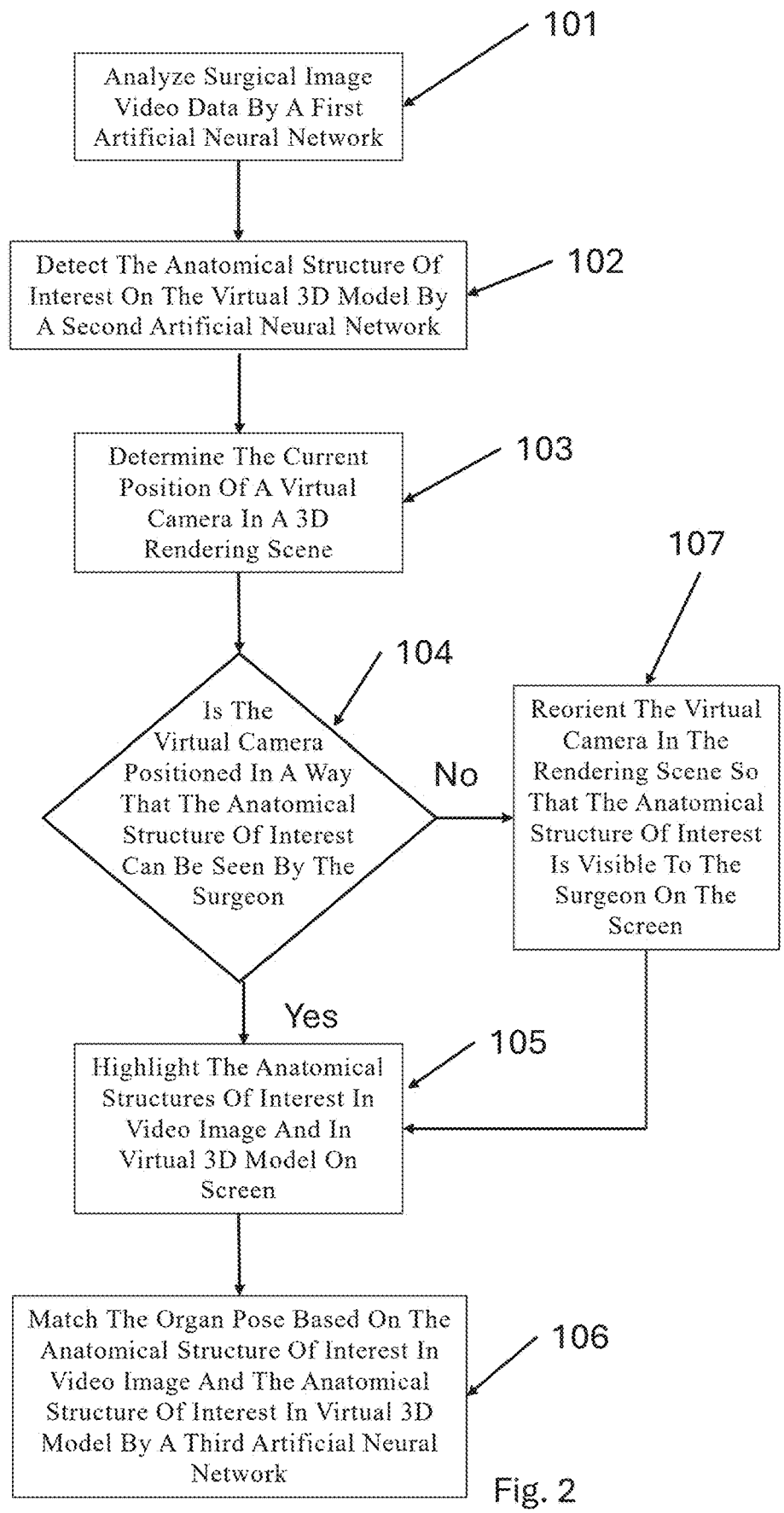
FIG. 2 illustrates a schematic workflow of a method for operating a medical navigation system for an image-guided surgical (IGS) procedure according to one embodiment.

FIG. 2 shows a schematic workflow of a method for operating a medical navigation system for an image-guided surgical (IGS) procedure according to one embodiment.

After capturing an image of a target object of a patient by a digital video sensor during a surgery, with e.g., a laparoscope, the set of the surgical image video data are analyzed by a first artificial neural network in step 101, wherein the anatomical structure of interest, like landmarks in the image, is detected and identified on the video image.

In the second step 102, the anatomical structure of interest is detected on the virtual 3D model of the target object by a second artificial neural network.

Then in the next step 103, the current position of a virtual camera in a 3D rendering scene is determined. Afterwards, in the following step 104 the decision has to be made whether the virtual camera is positioned in a way that the anatomical structure of interest can be seen by the surgeon. In case Yes, in the step 105 the anatomical structures of interest in video image as well as in virtual 3D model are highlighted on the screen.

In case that the anatomical structure of interest cannot be seen by the surgeon on the monitor in step 105, then the method carries out step 107 to reorient the virtual camera in the rendering scene so that the anatomical structure of interest will become visible to the surgeon on the monitor.

Finally, in step 106 a matching of the organ pose is performed by a third artificial neural network, wherein the matching is based on the anatomical structure of interest in video image and the anatomical structure of interest virtual 3D model.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A method for operating a medical navigation system for an image-guided surgical procedure comprising:
    training of a first artificial neural network on a set of surgical image video data of a target object of a patient, which represents a video image, and identifying the structure of the target object of the patient;
    training of a second artificial neural network on at least one virtual three-dimensional target object model of the target object and identifying the structure of the virtual three-dimensional target object model by the structure of the target object of the patient, which is identified by the first artificial neural network;
    training of a third artificial neural network by the identified structure of the target object of the patient and the structure of the virtual three-dimensional target object model and aligning the structure of the target object of the patient, which is identified by the first artificial neural network, with the structure of the corresponding target object of the virtual three-dimensional target object model, which is identified by the second artificial neural network;
    displaying the set of surgical image video data on a monitor and displaying the structure of the virtual three-dimensional target object model, which is identified by the second artificial neural network on a monitor; and
    detecting a landmark in the set of surgical image video data that triggers the second artificial neural network for training on the virtual three-dimensional model.

2. The method according to claim 1, wherein the set of surgical image video data is captured by a video processor.

3. The method according to claim 2, wherein the displaying comprises, displaying the set of surgical image video data in a predetermined orientation and displaying the structure of the virtual three-dimensional target object model, which is identified by the second artificial neural network in an orientation which corresponds or aligns with the predetermined orientation of the surgical image video data.

4. The method according to any of claim 1, wherein the second artificial neural network is configured to be trained on virtual three-dimensional models of the target object of the patient in order to learn and identify a corresponding landmark of the landmark, which is identified by the first artificial neural network, in the structure of the virtual three-dimensional target object model.

5. The method according to claim 4, wherein in case that the corresponding landmark in the structure of the virtual three-dimensional target object model cannot be displayed due to a hidden pose of the corresponding landmark in the structure of the virtual three-dimensional target object model, the method further comprising repositioning the structure of the virtual three-dimensional target object model such that the structure of the virtual three-dimensional target object model with the corresponding landmark is displayed on a monitor.

6. The method according to claim 1, wherein the third neural network is configured to be trained to match a pose of the landmark in the set of surgical image video data in order to align the structure of the target object of the patient, which is identified by the first artificial neural network, with the structure of the virtual three-dimensional target object model, which is identified by the second artificial neural network.

7. The method according to claim 1, wherein the first artificial neural network is an object recognition network, the object recognition network is configured to learn representations of key anatomical structures of the target object of the patient, and the representations are intraoperative representations.

8. The method according to claim 1, wherein the second artificial neural network is an object recognition network, the object recognition network is configured to learn representations of anatomical structures of the target object of the patient in different virtual three-dimensional models.

9. The method according to claim 1, wherein the third artificial neural network is configured to determine world coordinates of the different virtual three-dimensional model with respect to the orientation of the anatomical structures of the target object of the patient in the virtual three-dimensional model.

10. Non-transitory computer-readable storage medium storing instructions that cause a computer to:
   train of a first artificial neural network on a set of surgical image video data of a target object of a patient, which represents a video image, and identifying the structure of the target object of the patient;
   train of a second artificial neural network on at least one virtual three-dimensional target object model of the target object and identifying the structure of the virtual three-dimensional target object model by the structure of the target object of the patient, which is identified by the first artificial neural network;
   train of a third artificial neural network by the identified structure of the target object of the patient and the structure of the virtual three-dimensional target object model and aligning the structure of the target object of the patient, which is identified by the first artificial neural network, with the structure of the corresponding target object of the virtual three-dimensional target object model, which is identified by the second artificial neural network;
   displaying the set of surgical image video data on a monitor and displaying the structure of the virtual three-dimensional target object model, which is identified by the second artificial neural network on a monitor; and
   detecting a landmark in the set of surgical image video data that triggers the second artificial neural network for training on the virtual three-dimensional model.

11. A method for operating a medical navigation system for an image-guided surgical procedure comprising:
   training of a first artificial neural network on surgical image video data of a target object of a patient and identifying the structure of the target object of the patient;
   acquiring a segmentation layer of a predetermined identified structure of the target object of the patient; and
   training of a further artificial neural network by the structure of the target object of the patient, identified by the first artificial neural network, and the predetermined identified structure of the target object of the patient, provided by the segmentation layer, and aligning the structure of the target object of the patient, identified by the first artificial neural network, with the predetermined structure of the corresponding target object, provided by the segmentation layer;
   wherein an automatically detected landmark in the surgical image video data, detected by the first artificial neural network, is detected by the first artificial neural network in a static mode or in real-time; and
   the detected landmark in the surgical image video data is highlighted and displayed on a monitor.

12. The method according to claim 11, wherein the set of surgical image video data is captured by a video processor.

13. The method according to claim 12, further comprising displaying the set of surgical image video data in a predetermined orientation and displaying the predetermined structure of the target object in an orientation, which corresponds or aligns with the predetermined orientation of the surgical image video data.

14. The method according to claim 11, further comprising displaying the set of surgical image video data on the monitor and displaying the predetermined structure of the target object, provided by the segmentation layer on a monitor.

15. The method according to claim 11, wherein the segmentation layer comprises meta data of a computed tomography image of the target object of the patient, wherein the meta data represent the predetermined identified structure of the target object of the patient.

16. The method according to claim 11, wherein in case that the predetermined identified structure of the target object of the patient cannot be displayed due to a hidden pose of the predetermined identified structure of the target object of the patient, the method further comprising repositioning the predetermined identified structure of the target object of the patient such that the predetermined identified structure of the target object of the patient is displayed on the monitor.

17. The method according to claim 11, wherein the further neural network is configured to be trained to match a pose of the landmark in the set of surgical image video data in order to align the structure of the target object of the patient, which is identified by the first artificial neural network, with the predetermined identified structure of the target object of the patient, provided by the segmentation layer.

18. The method according to claim 11, wherein the first artificial neural network is an object recognition network, wherein the object recognition network is configured to learn representations of key anatomical structures of the target object of the patient,
   wherein the representations are intraoperative representations.

19. The method according to claim 11, wherein the further artificial neural network is configured to determine world coordinates of the different virtual three-dimensional model with respect to the orientation of the anatomical structures of the target object of the patient in the virtual three-dimensional model.

20. Non-transitory computer-readable storage medium storing instructions that cause a computer to:
   train of a first artificial neural network on surgical image video data of a target object of a patient and identifying the structure of the target object of the patient;
   acquire a segmentation layer of a predetermined identified structure of the target object of the patient; and
   train of a further artificial neural network by the structure of the target object of the patient, identified by the first artificial neural network, and the predetermined identified structure of the target object of the patient, provided by the segmentation layer, and aligning the structure of the target object of the patient, identified by the first artificial neural network, with the predetermined structure of the corresponding target object, provided by the segmentation layer;

wherein an automatically detected landmark in the surgical image video data, detected by the first artificial neural network, is detected by the first artificial neural network in a static mode or in real-time; and the detected landmark in the set of surgical image video data is highlighted and displayed on a monitor.

* * * * *